United States Patent
Welss et al.

(10) Patent No.: US 10,292,919 B2
(45) Date of Patent: May 21, 2019

(54) ORAL AND DENTAL HYGIENE AND CLEANING PRODUCTS WITH AN ARGININE DERIVATIVE FOR IMPROVED PLAQUE REMOVAL

(71) Applicant: Henkel AG & Co. KGaA, Duesseldorf (DE)

(72) Inventors: Thomas Welss, Duesseldorf (DE); Nicole Duschek, Duesseldorf (DE); Kristin Miehlich, Wuppertal (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 9 days.

(21) Appl. No.: 15/531,933

(22) PCT Filed: Dec. 3, 2015

(86) PCT No.: PCT/EP2015/078451
§ 371 (c)(1),
(2) Date: May 31, 2017

(87) PCT Pub. No.: WO2016/091702
PCT Pub. Date: Jun. 16, 2016

(65) Prior Publication Data
US 2017/0326053 A1    Nov. 16, 2017

(30) Foreign Application Priority Data

Dec. 10, 2014  (DE) .................. 10 2014 225 427

(51) Int. Cl.
*A61K 8/44* (2006.01)
*A61Q 11/00* (2006.01)
*A61K 8/19* (2006.01)
*A61K 8/21* (2006.01)

(52) U.S. Cl.
CPC ............... *A61K 8/44* (2013.01); *A61K 8/19* (2013.01); *A61K 8/21* (2013.01); *A61Q 11/00* (2013.01); *A61K 2800/87* (2013.01)

(58) Field of Classification Search
CPC ...................................................... A61K 8/44
See application file for complete search history.

(56) References Cited

U.S. PATENT DOCUMENTS

| 3,413,326 A | 11/1968 | Schmid et al. |
| 4,477,429 A | 10/1984 | Silbering et al. |
| 2004/0258630 A1 | 12/2004 | Boyd et al. |

FOREIGN PATENT DOCUMENTS

| EP | 1584320 A1 | 10/2005 |
| EP | 2377848 A1 | 10/2011 |
| EP | 2591766 A2 | 5/2013 |
| WO | 2012057739 A1 | 5/2012 |

OTHER PUBLICATIONS

EPO, International Search Report and Written Opinion issued in International Application No. PCT/EP2015/078451, dated Feb. 15, 2016.

*Primary Examiner* — Benjamin J Packard
(74) *Attorney, Agent, or Firm* — Lorenz & Kopf, LLP

(57) ABSTRACT

Oral and dental care and cleaning agents and methods that employ the agents are provided herein. In an embodiment, an oral and dental care and cleaning agent includes a polyol derivative of arginine. In another embodiment, a method includes the steps of supplying a toothbrush having a brush head and applying an agent to the brush head, wherein the agent includes a polyol derivative of arginine. Teeth are cleaned using the agent on the brush head.

20 Claims, No Drawings

ORAL AND DENTAL HYGIENE AND CLEANING PRODUCTS WITH AN ARGININE DERIVATIVE FOR IMPROVED PLAQUE REMOVAL

CROSS-REFERENCE TO RELATED APPLICATION

This application is a U.S. National-Stage entry under 35 U.S.C. § 371 based on International Application No. PCT/EP2015/078451, filed Dec. 3, 2015 which was published under PCT Article 21(2) and which claims priority to German Application No. 102014225427.2, filed Dec. 10, 2014, which are all hereby incorporated in their entirety by reference.

TECHNICAL FIELD

The present disclosure relates to oral and dental care and cleaning agents with an arginine derivative for gentle and effective cleaning of teeth.

BACKGROUND

Dental cleaning agents are available in various forms on the market and serve primarily to clean the tooth surface and prevent dental and gingival diseases. They usually contain a combination of polishing agents, humectants, surfactants, binders, flavorings and both antimicrobial and fluoride active ingredients. In addition to tooth powders, which play a subordinate role because of their high level of abrasiveness, dental cleaning agents are offered mainly in the form of pastes, creams and translucent or transparent gels. In recent years, liquid dental creams and mouthwashes have also become increasingly important.

It is generally acknowledged that there is a causal relationship between the presence of plaque and in particular calculus and various disease of the gingiva such as cavities, gingivitis, halitosis or periodontitis.

The basis for suitable prophylaxis is considered to be tooth brushing twice or more each day to at least suppress unwanted development of plaque on the tooth surfaces and bacterial invasion of the oral cavity as a whole.

However even a few minutes after tooth brushing the development of a new so-called pellicle layer can be detected on the tooth surface. This is a deposit of proteins from saliva. The pellicle layer is not very objectionable per se for the healthy teeth but then additional microorganisms from the salivary flora begin to grow on the pellicle layer, leading to an increase in the thickness of the resulting biofilm. This is where harmful microorganisms can also begin to grow. A matrix of extracellular polymer substances (EPS) capable of embedding a variety of bacterial species in the tooth surface can then develop. The resulting cell layer is referred to as plaque, which promotes the development of caries. The polysaccharides contained in the plaque in addition to low-molecular sugars form a source of nutrients for the embedded bacteria. These bacteria then gradually degrade the polysaccharides to acidic degradation products such as pyruvic acid and lactic acid. The resulting drop in pH causes degradation of dentin, which is also known as caries.

The uptake and incorporation of inorganic substances (mineral substances) from saliva can result in the formation of dental calculus from the plaque. This cannot usually be removed by a toothbrush. Dental calculus promotes the development of the diseases of the gingiva mentioned above.

EP 2591766 A2 describes an oral and dental care and cleaning agent containing a selected polyamine capable of reducing dental calculus.

However, there is still a need for reducing dental calculus, combatting the resulting diseases and providing active ingredients for this purpose. There is also the goal of improving oral and dental care and cleaning agents accordingly.

BRIEF SUMMARY

Oral and dental care and cleaning agents and methods that employ the agents are provided herein. In an embodiment, an oral and dental care and cleaning agent includes a polyol derivative of arginine.

In another embodiment, a method includes the steps of supplying a toothbrush having a brush head and applying an agent to the brush head, wherein the agent includes a polyol derivative of arginine. Teeth are cleaned using the agent on the brush head.

In another embodiment, an oral and dental care and cleaning agent includes a polyol derivative of arginine having a structure of formula (I):

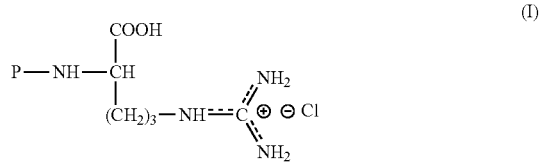

in which P denotes a polyol radical and wherein the polyol is selected from the group of glycerol, sorbitol, hexanediol, xylitol, erythritol, and mixtures thereof. The polyol derivative of arginine is present in an amount of from about 0.01 to about 5 wt %, based on the weight of the polyol derivative of arginine. The agent further includes fluoride and calcium carbonate.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has surprisingly been found that the goals described above can be achieved by using polyol derivatives of arginine.

Use of arginine in oral and dental care agents is known per se. For example, U.S. Pat. No. 3,413,326 describes the use of HF addition products onto arginine as anti-caries compounds in toothpastes. WO 2012/57739 A1 describes toothpastes containing a combination of arginine and calcium carbonate, which are suitable for the cleaning and care of hypersensitive teeth in particular.

The oral and dental care and cleaning agents comprising polyol derivatives or arginine have a surprisingly good effect in inhibition, reduction and dissolution (elimination) of biofilms on tooth surfaces. The new formation of pellicle layer is thereby modified to the extent that it is difficult for bacteria to adhere to the cleaned tooth surfaces. Furthermore, any extracellular polymer structures (EPS) that might be present are dissolved. In addition, a reduction in pH at the tooth surface is prevented or at least is definitely diminished.

The subject matter of the present disclosure in a first embodiment is an oral and dental care and cleaning agent containing a polyol derivative of arginine.

Oral and dental care agents as well as oral and dental cleaning agents as contemplated herein are oral and tooth powders, oral and toothpastes, liquid oral and dental creams, oral and dental rinses as well as oral and dental gels. Toothpastes and liquid dental cleaning agents are preferred. For example, the oral and dental care and cleaning agents may therefore be present in the form of toothpastes, liquid dental creams, tooth powders, mouthwashes or optionally also as a chewing composition, for example, chewing gum. However, they are preferably in the form of more or less flowable or plastic toothpastes such as those used for cleaning teeth with a toothbrush. Another particularly preferred embodiment of the present disclosure comprises mouthwash solutions and rinses, which are used for rinsing out the oral cavity.

These agents contain as an essential ingredient a polyol derivative of arginine.

Arginine is a proteinogenous α-amino acid with a guanidine functionality in the side chain. The guanidine group is protonated in both acidic and neutral media as well as in a weakly basic medium and has a positive charge which is delocalized between the amino groups.

The arginine in the polyol derivative is connected to a polyol radical by the free $NH_2$ group. The polyol radical is preferably derived from glycerol, sorbitol, hexane diol, xylitol and erythritol, but a glycerol radical is preferred.

The polyol derivatives of arginine can be obtained, for example, by reacting the alcohols, the amino acid and hydrogen in the presence of hydrogenation catalysts.

The polyol derivatives of arginine are preferably used in the hydrochloride form. Accordingly, in a preferred embodiment, the polyol derivatives of arginine have a structure of formula (I):

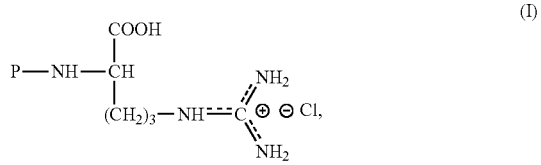

(I)

where P stands for a polyol radical, in particular for a glycerol, sorbitol, hexane diol, xylitol or erythritol radical.

In a particularly preferred embodiment, the P radical is derived from glycerol and the polyol derivative of arginine has a structure of formula (Ia):

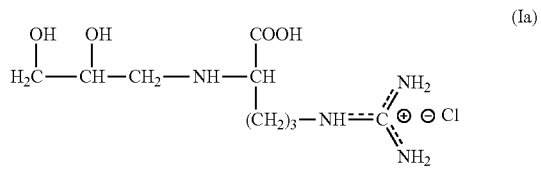

(Ia)

A preferred polyol derivative of arginine is known under the INCI designation dihydroxypropyl arginine HCl, for example. This polyol derivative of arginine is commercially available under the name Amitose R from the company Seiwa Kasei.

Preferred oral and dental care and cleaning agents use the polyol derivative of arginine within narrow quantity ranges. Oral and dental care and cleaning agents that contain, based on their weight, from about 0.01 to about 5 wt %, preferably from about 0.1 to about 4 wt %, especially preferably from about 0.5 to about 3 wt % and extremely preferably from about 1 to about 2.5 wt % polyol derivative of arginine, are preferred here.

Without being limited to this theory, the polyol derivatives of arginine are better stabilized than arginine in the oral and dental care and cleaning agents and thus also have an improved performance against bacteria and/or plaque. The polyol derivatives of arginine become embedded in the plaque, where they are cleaved enzymatically into arginine and polyol, and in particular the arginine can then act on site.

The oral and dental care and cleaning agents contain additional ingredients. The use of fluoride is especially preferred here. This may be supplied in the form of inorganic fluoride salts (sodium fluoride, tin(II) chloride, sodium monofluoride phosphate, etc.). Amine fluorides such as olaflur are also suitable.

It has been found that the deposition of fluoride can be increased by the presence of a polyol derivative of arginine in the agents above a certain fluoride content. The minimum amount of fluoride is about 500 ppm. Below this limit, the use of the polyol derivatives of arginine does not have a noticeable effect on fluoride deposition. Especially good fluoride deposition values are achieved when the polyol derivatives of arginine are used in the presence of larger amounts of fluoride, with amounts of about 1000 ppm fluoride or more having been found to be especially preferred.

Especially preferred oral and dental care and cleaning agents contain from about 1225 to about 1575 ppm, preferably from about 1250 to about 1550 ppm, more preferably from about 1275 to about 1525 ppm, even more preferably from about 1300 to about 1500 ppm, even more preferably from about 1325 to about 1475 ppm and in particular from about 1350 to about 1450 ppm fluoride.

If fluoride is supplied in the form of sodium fluoride, then 1 wt % sodium fluoride corresponds to approximately 4524 ppm fluoride, so that preferred agents contain from about 0.27 to about 0.35 wt %, preferably from about 0.28 to about 0.34 wt %, more preferably from about 0.29 to about 0.33 wt % and in particular from about 0.30 to about 0.32 wt % sodium fluoride.

As additional important ingredients, the agents may contain from about 0.01 to about 10 wt % anionic surfactant(s). Especially preferred oral and dental care and cleaning agents contain from about 0.5 to about 5 wt %, preferably from about 0.75 to about 3 wt % and in particular from about 1 to about 2.5 wt % anionic surfactant(s).

Typical examples of anionic surfactants include soaps, alkyl benzene sulfonates, alkane sulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfo succinates, mono- and dialkyl sulfo succinamates, sulfo triglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligo glucoside sulfates, protein fatty acid condensates (in particular plant products based on wheat) and alkyl (ether) phosphates. If the anionic surfactants contain polyglycol ether chains, these may have a conventional but preferably narrow homolog distribution.

Most especially preferred agents contain alkyl sulfate(s) as the anionic surfactant. Especially preferred oral and dental care agents here contain, based on their weight, from about 0.5 to about 2.5 wt %, more preferably from about 0.75 to about 2 wt % and in particular preferably from about 1.0 to about 1.5 wt % sodium lauryl sulfate.

Especially preferred agents also contain fatty alcohol ether sulfates as the anionic surfactant. Preferred fatty alcohol ether sulfates are those of the formula:

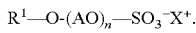

$R^1$—O-(AO)$_n$—SO$_3^-$X$^+$.

In this formula, $R^1$ stands for a linear or branched substituted or unsubstituted alkyl radical, preferably a linear, unsubstituted alkyl radical, especially preferably a fatty alcohol radical. Especially preferred radicals $R^1$ are selected from decyl, undecyl, dodecyl, tridecyl, tetradecyl, pentadecyl, hexadecyl, heptadecyl, octadecyl, nonadecyl, eicosyl radicals and mixtures thereof, wherein the representatives with an even number of carbon atoms are preferred. Especially preferred $R^1$ radicals are derived from $C_{12}$-$C_{18}$ fatty alcohols, for example, coconut fatty alcohol, tallow fatty alcohol, lauryl, myristyl, cetyl or stearyl alcohol or $C_{10}$-$C_{20}$ oxoalcohols.

AO stands for an ethylene oxide (EO) group or a propylene oxide (PO) group, preferably an ethylene oxide group. The index n stands for an integer from about 1 to about 50, preferably from about 1 to about 20 and in particular from about 2 to about 10. Most especially preferably n stands for the numbers 2, 3, 4, 5, 6, 7 or 8. X stands for a monovalent cation or the $n^{th}$ part of an n-valent cation. The alkali metal ions and, of them, Na$^+$ or K$^+$, are preferred, and Na$^+$ is extremely preferred. Other X$^+$ cations can be selected from NH$_4^+$, 1/2Zn$^{2+}$, 1/2Mg$^{2+}$, 1/2Ca$^{2+}$, 1/2Mn$^{2+}$ and mixtures thereof.

Especially preferred oral and dental care and cleaning agents contain a fatty alcohol ether sulfate selected from fatty alcohol ether sulfates of the formula:

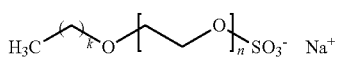

where k=11 to 19, n=2, 3, 4, 5, 6, 7 or 8. Most especially preferred representatives include $C_{12-14}$ fatty alcohol ether sulfates with two EO groups (k=11-13, n=2) and in particular their Na salts. The stated degree of ethoxylation constitutes a statistical average which may be an integer or a fraction for a specific product.

Especially preferred oral and dental care and cleaning agents here contain from about 0.5 to about 2.5 wt %, more preferably from about 0.75 to about 2 wt % and in particular preferably from about 1.0 to about 1.5 wt % sodium lauryl ether sulfate with two EO groups.

Use of so-called humectants which prevent toothpastes from drying out and increase the efficacy of the polyol derivatives of arginine is also especially preferred. In so-called liquid dental creams with a flowable rheology, these humectants serve as a matrix and are used in larger amounts. In mouthwashes and mouth rinses, these humectants are used to regulate consistency and as additional sweeteners. Suitable humectants include in particular a polyvalent alcohol from the group of sorbitol and/or glycerol and/or 1,2-propylene glycol.

Oral and dental care and cleaning agents that contain, based on their weight, from about 0.5 to about 7 wt %, preferably from about 0.75 to about 60 wt %, especially preferably from about 1 to about 50 wt % and in particular from about 2 to about 40 wt % of at least one polyvalent alcohol selected from the group of sorbitol, glycerol, 1,2-propylene glycol and mixture thereof are preferred.

For certain fields of application, it may be advantageous to use only one of the three ingredients listed above. Sorbitol is preferred in most cases. However, mixtures of two of the three substances or all three substances may be preferred in other fields of application. A mixture of glycerol, sorbitol and 1,2-propylene glycol in a weight ratio of from about 1:(0.5-1):(0.1-0.5) has proven to be especially advantageous here.

In addition to sorbitol and/or glycerol and/or 1,2-propylene glycol, other polyvalent alcohols that have proven to be suitable include those with at least two OH groups, preferably mannitol, xylitol, polyethylene glycol, polypropylene glycol and mixtures thereof. Of these compounds, those with 2 to 12 OH groups and in particular those 2, 3, 4, 5, 6 or 10 OH groups are preferred.

Polyhydroxy compounds with two OH groups include for example glycol (CH$_2$(OH)CH$_2$OH) and other 1,2-diols such as H—(CH$_2$)$_n$—CH(OH)CH$_2$OH, where n=2, 3, 4, 5, 6, 7, 8, 9, 10, 11, 12, 13, 14, 15, 16, 17, 18, 19, 20. Also, 1,3-diols, such as H—(CH$_2$)$_n$—CH(OH)CH$_2$CH$_2$OH, where n=2, 3, 4, 5, 6, 7, 8, 9, 10, 11, 12, 13, 14, 15, 16, 17, 18, 19, 20 can be used. The (n, n+1)- and/or (n, n+2)-diols with nonterminal OH groups can also be used. Important representatives of polyhydroxy compounds with two OH groups also include polyethylene glycols and polypropylene glycols. As preferred additional polyvalent alcohols, for example, xylitol, propylene glycols, polyethylene glycols in particular those with average molecular weights of 200 to 800 may be used.

The agents may contain additional surfactant(s), in particular amphoteric surfactants as additional ingredients. The other surfactants are preferably used within narrow quantity ranges, so that preferred oral and dental care and cleaning agents contain from about 0.5 to about 5 wt %, preferably from about 0.75 to about 4.5 wt %, more preferably from about 1 to about 4 wt %, even more preferably from about 1.25 to about 3.5 wt % and in particular from about 1.6 to about 2.5 wt % surfactant(s).

Especially preferred oral and dental care and cleaning agents contain amphoteric surfactant(s) from the groups of
N-alkylglycines,
N-alkylpropionic acids,
N-alkylaminobutyric acids,
N-alkyliminodipropionic acids,
N-hydroxyethyl-N-alkylamidopropyl glycines,
N-alkyltaurines,
N-alkylsarcosines,
2-alkylaminopropionic acids each with approx. 8 to 24 carbon atoms in the alkyl group,
alkylaminoacetic acids each with approx. 8 to 24 carbon atoms in the alkyl group,
N-cocoalkyl aminopropionate,
cocoacylaminoethylaminopropionate,
$C_{12}$-$C_{18}$ acylsarcosine,
N-alkyl-N,N-dimethylammonium glycinates for example cocoalkyldimethyl-ammonium glycinate,
N-acylaminopropyl-N,N-dimethylammonium glycinates for example cocoacylaminopropyldimethylammonium glycinate,
2-alkyl-3-carboxymethyl-3-hydroxyethylimidazolines each with 8 to 18 carbon atoms in the alkyl or acyl group, Cocoacylaminoethylhydroxyethylcarboxymethyl glycinate, the compounds known by the INCI designation cocamidopropyl betaine, the compounds known with the INCI designation disodium cocoampho diacetates.

Especially preferred oral and dental care and cleaning agents contain betaines of the formula (Bet-I) as the amphoteric surfactants:

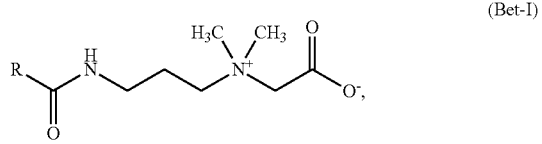

(Bet-I)

where R stands for linear or branched saturated or mono- and/or polyunsaturated alkyl or alkenyl radicals each with from about 8 to about 24 carbon atoms.

These surfactants are referred to according to the INCI nomenclature as amidopropyl betaines, wherein the representatives derived from coconut fatty acids are preferred and are referred to as cocamidopropyl betaines. Especially preferred surfactants of the formula (Bet-I), comprising a mixture of the following representatives, are used:

$H_3C-(CH_2)_7-C(O)-NH-(CH_2)_3N^+(CH_3)_2CH_2COO^-$
$H_3C-(CH_2)_9-C(O)-NH-(CH_2)_3N^+(CH_3)_2CH_2COO^-$
$H_3C-(CH_2)_{11}-C(O)-NH-(CH_2)_3N^+(CH_3)_2CH_2COO^-$
$H_3C-(CH_2)_{13}-C(O)-NH-(CH_2)_3N^+(CH_3)_2CH_2COO^-$
$H_3C-(CH_2)_{15}-C(O)-NH-(CH_2)_3N^+(CH_3)_2CH_2COO^-$
$H_3C-(CH_2)_7-CH=CH-(CH_2)_7-C(O)-NH-(CH_2)_3N+(CH_3)_2CH_2COO^-$.

Surfactants of the formula (Bet-I) are especially preferably used within narrow quantity ranges. The preferred oral and dental care and cleaning agents are those containing, based on their weight, from about 0.1 to about 4.0 wt %, preferably from about 0.2 to about 3.0 wt %, especially preferably from about 0.3 to about 2.5 wt %, more preferably from about 0.4 to about 2.0 wt % and in particular from about 0.5 to about 1.6 wt % cocamidopropyl betaine.

To manifest the cleaning performance and achieve a "natural" lightening of the color of teeth, the dental care and cleaning agents may contain polishing agents in particular. Suitable polishing agents include in principle the polishing agents that are suitable for dental care and cleaning agents. Preferred suitable polishing agent components include silicic acids, aluminum hydroxide, aluminum oxide, sodium aluminum silicates, organic polymers, calcium carbonate or mixtures of these cleaning substances.

Calcium-containing polishing components may also be present, for example, chalk, synthetic calcium carbonate, calcium pyrophosphate, dicalcium phosphate dihydrate may be used in amounts of up to about 5 wt %, based on the total agent.

The total polishing agent content is preferably in the range of from about 5-50 wt % of the dental care and cleaning agent.

Toothpastes and liquid dental cleaning agents containing silicic acids as the polishing agent are especially preferred. Suitable silicic acids include, for example, gel silicic acids, hydrogel silicic acids and precipitated silicic acids. Gel silicic acids are prepared by reaction of sodium silicate solutions with strong aqueous mineral acids, forming a hydrosol, aging to form the hydrogel, washing and drying. If the drying takes place under general conditions to yield water contents of from about 15 to about 35 wt %, then the so-called hydrogel silicic acids are obtained. There is irreversible shrinkage of the previously loose structure of the hydrogel to form the dense structure of the so-called xerogel by drying to a water content of less than about 15 wt %.

A second preferred suitable group of silicic acid polishing agents includes the precipitated silicic acids, which are obtained by precipitation of silicic acid from dilute alkali silicate solutions by adding strong acids under conditions, under which aggregation to form the sol and gel cannot occur. A precipitated silicic acid with a BET surface area of from about 15-110 $m^2/g$, a particle size of from about 0.5-20 µm, wherein at least about 80 wt % of the primary particles should be less than about 5 µm in size, and a viscosity in 30% glycerol water (1:1) dispersion of from about 30-60 Pas (20° C.) in an amount of from about 10-20 wt % of the toothpastes are especially preferred. Precipitated silicic acids of this type, which are especially suitable, also have round corners and edges and can be obtained under the brand name Sident® 12 DS (Evonik).

Other precipitated silicic acids of this type include Sident® 8 (Evonik) and Sorbosil® AC 39 (PQ Corp.). These silicic acids have a lower thickening effect and a somewhat higher average particle size of 8-14 µm with a specific surface area of 40-75 $m^2/g$ (according to BET) and are especially suitable for liquid dental creams. These should have a viscosity of from about 10-100 Pas (25° C., shear rate $D=10 \, s^{-1}$).

However, toothpastes having a definitely higher viscosity of more than 100 Pas (25° C., $D=10 \, s^{-1}$) need a sufficiently large amount of silicic acids with a particle size of less than 5 µm, preferably at least about 3 wt % of a silicic acid with a particle size of 1-3 µm. Therefore, in addition to the aforementioned precipitated silicic acids, so-called thickener silicic acids with an even smaller particle size and with a BET surface area of from about 150-250 $m^2/g$ are therefore preferably added to such toothpastes, for example, the commercial products Sipernat® 22 LS or Sipernat® 320 DS.

Likewise, aluminum oxide in the form of weakly calcined alumina with an aluminum oxide content in the amount of approx. 1-5 wt % may also be used as the polishing agent. Such a suitable aluminum oxide is available under the brand name "polishing aluminum P10 ultrafine" (Giulini Chemie). However, it is preferable for the aluminum oxide to also be used in the agents as an additional polishing agent, i.e., in combination with a polishing agent.

In addition, all the polishing materials known for toothpastes, such as sodium aluminum silicates, for example, zeolite A, organic polymers such as, for example, polymethacrylate or mixtures of these and the aforementioned polishing substances are also suitable.

In summary, oral and dental care and cleaning agents which additionally contain polishing substances, preferably silicic acids, aluminum hydroxide, aluminum oxide, calcium pyrophosphate, chalk, synthetic calcium carbonate, dicalcium phosphate dihydrate ($CaHPO_4.2H_2O$), sodium aluminum silicates, in particular zeolite A, organic polymers, in particular polymethacrylates or mixtures of these polishing substances, preferably in amounts of from about 1 to about 30 wt %, especially from about 2.5 to about 25 wt % and in particular from about 5 to about 22 wt %, each based on the total agent, are preferred.

The stated amounts refer to the total amount of polishing substances, wherein individual polishing substances may be used, preferably in narrower quantity ranges. Preferred agents contain, for example, from about 5 to about 20 wt %, preferably from about 8 to about 21 wt %, more preferably from about 9 to about 20 wt % and in particular from about 10 to about 19 wt % silicic acid(s). In addition to the silicic acid(s), other preferred agents contain from about 0.25 to about 2 wt %, preferably from about 0.5 to about 1.5 wt %, and in particular from about 0.75 to about 1.25 wt % aluminum oxide as an additional polishing agent.

It may also be preferable to use natural and/or synthetic calcium carbonate, in particular in combination with fluoride, as a polishing agent in the oral and dental care and cleaning agents.

The consistency regulators (and/or binders) may be, for example, natural and/or synthetic water-soluble polymers, such as alginates, carragheenates, gum tragacanth, starch and starch ethers, cellulose ethers, for example, carboxymethyl cellulose (Na salt), hydroxyethyl cellulose, methyl hydroxypropyl cellulose, guar gum, acacia gum, agar, xanthan gum, succinoglycan gum, carob bean gum, pectins, water-soluble carboxyvinyl polymers (for example, Carbopol® grades), polyvinyl alcohol, polyvinylpyrrolidone, polyethylene glycols, in particular those with molecular weights of from about 1500-1,000,000.

Additional substances that are suitable for regulating the viscosity include, for example, sheet silicates, such as montmorillonite clays, colloidal thickening silicic acids, for example, aerogel silicic acids, pyrogenic silicic acids or extremely finely ground precipitated silicic acids. Viscosity stabilizing additives from the group of cationic, zwitterionic or ampholytic nitrogen-containing surfactants, hydroxypropyl substituted hydrocolloids or polyethylene glycol/polypropylene glycol copolymers with an average molecular weight of from about 1000 to about 5000 or a combination of the aforementioned compounds are also used in the toothpastes.

CMC and xanthan gum have proven to be especially compatible with the additional active ingredients of the oral and dental care and cleaning agents. The effect is especially pronounced when using these thickeners. Especially preferred oral and dental care and cleaning agents are thus contain, based on their weight from about 0.2 to about 7.5 wt %, preferably from about 0.25 to about 5 wt %, especially preferably from about 0.3 to about 4 wt %, more preferably from about 0.4 to about 3 wt %, even more preferably from about 0.45 to about 2 wt % and in particular from about 0.5 to about 0.8 wt % carboxymethyl cellulose.

Additional preferred oral and dental care and cleaning agents contain, based on their weight, from about 0.15 to about 5 wt %, preferably from about 0.2 to about 2.5 wt %, especially preferably from about 0.25 to about 1 wt %, more preferably from about 0.3 to about 0.75 wt %, even more preferably from about 0.35 to about 0.6 wt % and in particular from about 0.4 to about 0.5 wt % xanthan gum.

The agents, in particular the dental care and cleaning agents, may also contain substances to increase the mineralizing potential, for example, calcium-based substances such as calcium chloride, calcium acetate and dicalcium phosphate dihydrate. The concentration of the calcium-containing substance depends on the solubility of the substance and the interaction with other substances contained in the oral and dental care and cleaning agent. In addition to the aforementioned obligatory components, the oral and dental care and cleaning agents may also contain additional additives and auxiliary substances that are essentially known. One additive that has long been known as a toothpaste component is particularly effective in the oral and dental care and cleaning agents: calcium glycerophosphate, which is the calcium salt of glycerol-1-phosphoric acid or glycerol-2-phosphoric acid or the glycerol-3-phosphoric acid that is an enantiomer of glycerol-1-phosphoric acid or a mixture of these acids. The compound has a remineralizing effect in dental care products because it supplies both calcium ions and phosphate ions. Calcium glycerophosphate is preferably used in oral and dental care and cleaning agents in amounts of from about 0.01-1 wt %. On the whole, the oral and dental care and cleaning agents may contain the usual additives and auxiliary substances in amounts up to about 10 wt %.

The organoleptic properties of these oral and dental care and cleaning agents can be improved by adding flavoring oils and sweeteners, for example.

Flavoring oils that may be used include all the natural and synthetic flavorings that are customary in oral and dental care agents. Natural flavorings may be included in the form of the natural essential oils isolated from herbs and spices as well as the individual components isolated from them.

Suitable flavorings include, for example, peppermint oil, curly mint oil, eucalyptus oil, anise oil, fennel oil, caraway oil, menthyl acetate, cinnamaldehyde, anethol, vanillin, thymol as well as mixtures of these components.

Suitable sweeteners include, for example, sodium saccharine, sodium cyclamate, sucrose, lactose, maltose, fructose.

Other conventional additives and auxiliary substances for toothpastes or dental creams and mouthwashes or mouthwash solutions include:
Solvents and solubilizers, for example, low monovalent or polyvalent alcohols or ethers, e.g., ethanol, 1,2-propylene glycol, diethylene glycol or butyl diglycol,
Coloring agents,
Buffer substances, e.g., primary, secondary or tertiary alkali phosphates or citric acids/sodium citrate,
Additional wound-healing or anti-inflammatory substances, e.g., allantoin, urea, azulene, chamomile active ingredients, acetyl salicylic acid derivatives or rhodanide,
Vitamins, for example, ascorbic acid, biotin or tocopherol,
Mineral acids, for example, manganese, zinc or magnesium salts or sodium phosphates.

Other subjects as contemplated herein include the use of polyol derivatives of arginine for dissolving and/or removing extracellular polymer substances (EPS) on tooth surfaces and/or dental calculus (plaque) and/or tartar as well as use of an oral and dental care and cleaning agent containing a polyol derivative of arginine for dissolving and/or removing extracellular polymer substances (EPS) onto surfaces and/or dental calculus (plaque) and/or tartar and/or for reducing and/or preventing a reduction in pH at the tooth surface and/or for remineralizing dentin and/or for preventing demineralization of dentin.

With respect to preferred embodiments of these applications what was said above regarding the agents also applies here mutatis mutandis.

These agents may be formulated as a toothpaste or as a dental cream. Another subject of the present disclosure is the use of agents in methods for cleaning teeth by employing manually operated or electric toothbrushes. In the case of electric toothbrushes, the agents have the additional advantage that they are effective even in small amounts and also do not have a negative effect on the mechanism of the electric brush head.

Another subject matter of the present disclosure is a method for cleaning teeth and dissolving or removing extracellular polymer substances (EPS) on tooth surfaces and/or removing plaque and/or tartar and/or for reducing and/or preventing a reduction in pH at the tooth surface and/or for remineralization of dentin and/or for preventing demineralization of dentin, including the steps:

i. Supplying a toothbrush having a brush head, preferably a toothbrush whose brush head can be set in motion;
ii. Applying from about 0.5 to about 5 g of an agent as contemplated herein to the brush head;
iii. from about 30 to about 300 seconds of cleaning the teeth using the agent, preferably using the brush head, which has been set in motion.

With respect to preferred embodiments of the method, what was said above regarding the agents also applies here, mutatis mutandis.

However, the following examples should illustrate the subject of the present disclosure without restricting it.

EXAMPLES

All data given in wt %.

TABLE 1

Toothpaste formulations

| | A | B | C | D | E | F |
|---|---|---|---|---|---|---|
| Sorbitol 70% | 55 | 55 | 45 | 60 | 65 | 70 |
| Dihydroxypropyl arginine HCl | 1 | 2.5 | 0.5 | 1 | 1 | 1.5 |
| Hydrated silica | 12 | 20 | 10 | 5 | 12.5 | 14 |
| Sodium fluoride | 0.32 | 0.32 | 0.32 | 0.32 | 0.32 | 0.1 |
| Sodium saccharine | 0.25 | 0.25 | 0.1 | 0.5 | 0.2 | 0.25 |
| Ethanol | — | — | — | 1 | 2 | — |
| Xanthan | 0.6 | 0.6 | 0.3 | 0.2 | 0.2 | 0.1 |
| Sodium lauryl sulfate | 1.5 | 0.5 | 1.5 | 1.2 | 0.8 | 1.2 |
| Cocamidopropyl betaine | 1.3 | 1.3 | 0.6 | 0.6 | 0.6 | 0.6 |
| PEG-8 | 1.5 | 1.0 | 2.5 | 4.0 | 1.0 | 3.0 |
| Na$_2$HPO$_4$ | 0.2 | 0.2 | 0.2 | 0.2 | 0.5 | 0.2 |
| Flavoring | 1.1 | 1.1 | 0.75 | 1.5 | 0.5 | 0.75 |
| Water, coloring agent and optionally preservative | | | to 100 | | | |

TABLE 2

Mouthwash formulation

| | A | B | C | D | E | F |
|---|---|---|---|---|---|---|
| Sorbitol 70% | 1 | 1.5 | 2 | 2.5 | 3 | 5 |
| Dihydroxypropyl arginine HCl | 0.75 | 3.0 | 2.5 | 5 | 0.5 | 1 |
| Hydrated silica | 1 | 1.5 | 2 | 2.5 | 1 | 1 |
| Sodium fluoride | 0.11 | 0.11 | 0.11 | 0.11 | 0.11 | 0.11 |
| Sodium saccharine | 0.03 | 0.05 | 0.1 | 0.05 | 0.05 | 0.1 |
| PEG-60 hydrogenated castor oil | 0.2 | 0.2 | 0.2 | 0.2 | 0.2 | 0.2 |
| Trisodium dihydrate | 0.1 | 0.2 | 0.3 | 0.2 | 0.1 | 0.1 |
| Citric acid | 0.001 | 0.002 | 0.1 | 0.2 | 0.01 | 0.01 |
| Cetylpyridinium chloride | 0.01 | 0.1 | 0.05 | 0.05 | 0.1 | 0.01 |
| Flavoring | 0.5 | 0.5 | 0.5 | 0.5 | 0.5 | 0.5 |
| Water | | | to 100 | | | |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oral and dental care and cleaning agent comprising a polyol derivative of arginine and fluoride.

2. The agent according to claim 1, comprising, based on its weight, from about 0.01 to about 5 wt % of the polyol derivative of arginine.

3. The agent according to claim 1, wherein the polyol derivative of arginine has a structure of formula (I):

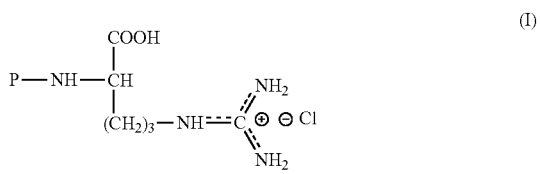

in which P denotes a polyol radical.

4. The agent according to claim 1, wherein the polyol is selected from the group of glycerol, sorbitol, hexanediol, xylitol, erythritol, and mixtures thereof.

5. The agent according to claim 1, wherein the polyol derivative of arginine has a structure of formula (Ia):

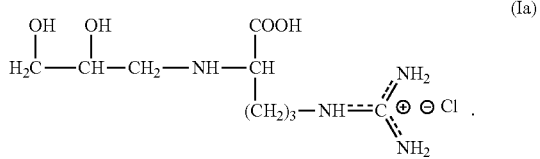

6. The agent according to claim 1, wherein the agent additionally comprises from about 500 to about 1600 ppm fluoride.

7. The agent according to claim 1, wherein the agent additionally comprises calcium carbonate.

8. A method comprising the steps of:
i. supplying a toothbrush having a brush head;
ii. applying an agent to the brush head, wherein the agent comprises a polyol derivative of arginine;
iii. cleaning teeth using the agent on the brush head.

9. The method according to claim 8, wherein applying the agent comprises applying from about 0.5 to about 5 g of the agent to the brush head.

10. The method according to claim 9, wherein cleaning the teeth using the agent on the brush head comprises cleaning the teeth for a period of from about 30 to about 300 seconds.

11. The method according to claim 8, wherein an extracellular polymer substance (EPS) is present on the teeth, and wherein cleaning the teeth comprises cleaning the teeth having the EPS substance on the teeth using the agent on the brush head.

12. The method according to claim 8, wherein cleaning the teeth comprises cleaning plaque and/or tartar from the teeth using the agent on the brush head.

13. The method according to claim 8, wherein cleaning the teeth comprises reducing and/or preventing a reduction in pH at the tooth surface using the agent on the brush head.

14. The method according to claim 8, wherein cleaning the teeth comprises remineralizing dentin and/or preventing demineralization of dentin using the agent on the brush head.

15. The agent according to claim 1, comprising, based on its weight, from about 1 to about 2.5 wt % of the polyol derivative of arginine.

16. The agent according to claim 3, wherein the polyol is selected from the group of glycerol, sorbitol, hexanediol, xylitol, erythritol, and mixtures thereof.

17. The agent according to claim 3, wherein the agent additionally comprises calcium carbonate and from about 500 to about 1600 ppm fluoride.

18. An oral and dental care and cleaning agent comprising:
a polyol derivative of arginine having a structure of formula (I):

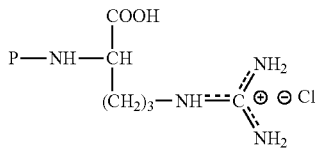

(I)

in which P denotes a polyol radical and wherein the polyol is selected from the group of glycerol, sorbitol, hexanediol, xylitol, erythritol, and mixtures thereof;
wherein the polyol derivative of arginine is present in an amount of from about 0.01 to about 5 wt %, based on the weight of the polyol derivative of arginine;
fluoride; and
calcium carbonate.

19. The agent according to claim 18, wherein the fluoride is present in an amount of from about 500 to about 1600 ppm.

20. The agent according to claim 18, wherein the polyol derivative of arginine has a structure of formula (Ia):

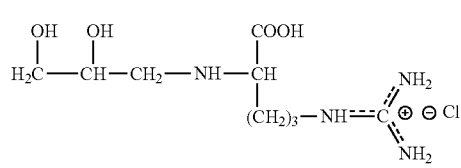

(Ia)

* * * * *